United States Patent [19]

Asano et al.

[11] Patent Number: 4,968,671
[45] Date of Patent: Nov. 6, 1990

[54] THERAPEUTIC AGENTS FOR ISCHEMIC HEART DISEASES

[75] Inventors: Masaharu Asano; Wataru Uchida; Kumiko Shibasaki, all of Tokyo, Japan

[73] Assignee: Yamanouchi Pharmaceutical Co., Ltd., Tokyo, Japan

[21] Appl. No.: 275,217

[22] Filed: Nov. 23, 1988

[30] Foreign Application Priority Data

Nov. 26, 1987 [JP] Japan .................................. 62-298759

[51] Int. Cl.$^5$ ............................................. A61K 37/02
[52] U.S. Cl. ....................................................... 514/18
[58] Field of Search ........................................... 514/18

[56] References Cited

FOREIGN PATENT DOCUMENTS

| 204589 | 12/1986 | European Pat. Off. | 514/18 |
| 249401 | 12/1987 | European Pat. Off. | 514/18 |
| 257992 | 3/1988 | European Pat. Off. | 514/18 |
| 249997 | 11/1986 | Japan | 514/18 |

Primary Examiner—Robert Gerstl
Attorney, Agent, or Firm—Burgess, Ryan & Wayne

[57] ABSTRACT

Therapeutic agents for ischemic heart diseases are provided and contain as an effective component a glutathione monoalkyl ester. The invention is also directed to the use of such therapeutic agents for the treatment of ischemic heart diseases.

3 Claims, No Drawings

THERAPEUTIC AGENTS FOR ISCHEMIC HEART DISEASES

DETAILED DESCRIPTION OF THE INVENTION

1. Field of Industrial Application

The present invention relates to therapeutic agents for ischemic heart diseases comprising as an effective component a glutathione monoalkyl ester represented by the general formula (I):

wherein R represents an alkyl, group, or a salt thereof.

2. Discussion of the Prior Art

Recently, in the field of diseases of the circulary system, the number of patients suffering from ischemic heart disease such as angina pectoris or myocardial infarction has been increasing. Among these, myocardial infarction has a high seriousness and, up to the present, various therapies have been studied. Most recently, therapeutics for these myocardial infarction, that is to say, PTCA and PTCR have been widely used in clinical therapy and their effectiveness have been recognized. Although these therapeutics are essential to healing the cardiac muscle from ischemic disorders, it has been disclosed that new disorders, for example, a dangerous ventricular arrhythmia such as ventriclular fibrillation due to occluded coronary artery reperfusion, hemorrhagic infarction or no-reflow (poor reperfusion) phenomena etc., appear irreversibly (See Braunwald and Kloner, J. Clin. Invest., 76, 1713-1719, 1985). However, since drugs having an effect for the treatment of these new disorders are unsatisfactory, there had been a need to develop new drugs.

SUMMARY OF THE INVENTION

The inventors of the present application have conducted studied to develop therapeutic agents for ischemic heart disease, especially drugs for controlling disorders which accompany occluded coronary artery reperfusion. As a result, it has been found that the glutathione monoalkyl esters possess an extremely marked effect for treatment of these diseases and the present invention has been accomplished.

Namely, the applicant of the present application has filed patent applications (Japanese patent appln. Nos. (Sho) 61-131313 and 196006) which disclosed that glutathione monoalkyl esters are useful as anti-anemic agents and prophylactic agents for cerebral ischemia. However, the present invention directed to therapeutic agents for ischemic heart diseases is quite dissimilar to the above-mentioned inventions in the kind of diseases applicable and the range of application for use.

DETAILED DESCRIPTION OF THE INVENTION

In the glutathione monoalkyl ester represented by general formula (I) described above, the alkyl group is a straight or branched group having 1 to 10 carbon atoms. Specific examples include methyl group, ethyl group, propyl group, isopropyl group, butyl group, isobutyl group, tert-butyl group, pentyl group, isopentyl group, neopentyl group, tert-pentyl group, 1-methylbutyl group, hexyl group, isohexyl group, 2-methylpentyl group, 1-ethylbutyl group, heptyl group, octyl group, nonyl group, decyl group, etc. The compound (I) or salts thereof can be produced, for example, by the following process:

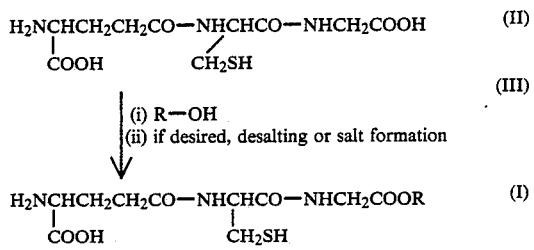

wherein R has the significance described above. Namely, the process can be carried out by reacting glutathione (II) with an alcohol (III) in the presence of an acid (for example, sulfuric acid) to produce salts of the glutathione monoalkyl ester and then, if desired, further desalting or subjecting the salts to a salt formation treatment.

The compound (I) of the present invention is administered preferably in its free form. The compound may also be administered in the form of salts with inorganic acids such as hydrochlorides, nitrates, sulfates, etc. or salts with organic acids such as oxalates, p-toluenesulfonates, maleates, etc. When the compound is administered in the form of the salt thereof, the salt can be desalted, if necessary, or, after a base such as sodium hydrogencarbonate that does not adversely affect the living body is added thereto.

The glutathione monoalkyl ester (I) or salts thereof in accordance with the present invention can be prepared into tablets, powders, granulates, granules, capsules, pills, liquids, injections, etc. using pharmaceutically acceptable carriers for medical preparations conventionally employed, which are orally or parenterally administered. Dose may be appropriately varied depending upon administration route, body weight, age, conditions, etc. of the patient.

The administration route and dose is continuously carried out by means of continuous injection into vein over the period of one to two hours before the operation, during the operation and after the operation for reopening the occluded coronary artery, from immediately after the emergency admission into a hospital due to myocardial infarction. Depending on the degree of seriousness, it is preferable to combine a single administration of frequency. In the case of a single dose, the dosage for adults ranges 500 to 5,000 mg, preferably 1,000 to 3,000 mg to the adult each time and in the case of continuous administration, the dosage ranges 30 to 100 mg/min.

The compound (I) or salts thereof in accordance with the present invention have acute toxicity ($LD_{50}$) of approximately 5.3 g/kg in intraperitoneal injection to mice, for example, in the case of the isopropyl ester.

EFFECTS OF THE INVENTION

Drugs comprising as an effective component glutathione monoalkyl esters represented by general formula (I) or salts thereof according to the present invention exhibit the action of controlling disorders due to occluded coronary artery reperfusion in ischemic heart diseases and are useful as therapeutic agents for ischemic heart diseases.

EXAMPLES

Hereafter, the formulations of the therapeutic agents and the effect of treating ischemic heart diseases according to the present invention will be described in more detail with reference to the examples. As a reference example, the synthesis example of glutathione monoisopropyl ester used in the working examples is shown below.

EXAMPLE 1

(Formulation of injection)

Glutathione monoisopropyl ester sulfate was suspended in purified water in a concentration of 45 mg/ml and the suspension was cooled to 5° C. or below. About 2-fold mols of sodium hydrogencarbonate were added the ester sulfate to dissolve the ester sulfate. After adjusting pH to 4, the solution was diluted to a concentration of 40 mg/ml followed by aseptic filtration. The solution was charged by 25 ml each in each vial and freeze dried.

EXAMPLE 2

(Action of treating ischemic heart diseases)

The inhibitory action of glutathione monoisopropyl ester on ventricular extra systole occurred when the occluded coronary artery was reperfused in dogs was tested with the following method.

Method of measurement:

Measurement was carried out by partially modifying Gibsons' method (J. Cardiovasc. Pharmacol., 5, 517–524, 1983). Dogs (Mongrel, female and male, 9–18 kg) were anesthetized with pentobarbital, the chest was opened under artificial respiration. And then the left coronary artery anterior descending segmental branch was occluded for 60 minutes. Thereafter, a reperfusion was carried out for 20 minutes and then blood pressure and heart rate as well as the heart surface electrocardiogram were measured.

The glutathione monoisopropyl ester (GE) was intravenously administered in a single dose of 300 mg/kg 30 minutes after the coronary artery occlusion and and continuous injection was carried out in the amount of 10 mg/kg/min, i.v., until the completion of this test from 40 minutes after the coronary artery occlusion. The effect of an agent was evaluated by the number of the ventricular extra systole for a minute, which had been occured during the time period of reperfusion.

(Results)

The action of GE on the number of ventricular extra systole occurred during the coronary artery occlusion/referfusion in dogs which were anesthetized and the chest of which was opened is shown below.

| Drugs | Number of animal | Number of ventricular extra systole (counts/min) |
|---|---|---|
| Control group (group given with physiological saline) | 13 | 35.9 ± 10.2 |
| GE-treated group (300 mg/kg i.v. + 10 mg/kg/min. i.v.) | 9 | 10.0 ± 5.6* |

The values shown in Table represent the mean value ± the standard deviation.
*P < 0.05: This represents a significant difference as compared to the control group (Student't-test).

REFERENCE EXAMPLE

Production of glutathione monoisopropyl ester:

(1) To 800 mo of isopropyl alcohol was added 124 g of glutathione. While stirring, 42 ml of 95% sulfuric acid was dropwise added to the mixture. Heat generated but it was unnecessary to coo. About one hour later, the system became a homogeneous solution and glutathione monoisopropyl ester (isopropyl r-L-glutamyl-L-cysteinyl glycinate) sulfate crystals began to precipitate about 24 hours after. The stirring was further continued overnight.

The crystals were taken by filtration, washed with 200 ml of isopropyl alcohol and dried under reduced pressure to give 88.5 g of the sulfate. A part of the crystals was recrystallized from water-isopropyl alcohol mixture (mixing ratio, 1:5) and purified to provide a sample for analysis.

Melting point: 145–150°C.

| Elemental analysis (as $C_{13}H_{23}N_3O_6S \cdot \frac{1}{2}H_2SO_4 \cdot \frac{1}{2}H_2O$) | | | |
|---|---|---|---|
| C | H | N | S |
| Calcd. (%) 38.32 | 6.18 | 10.31 | 11.80 |
| Found (%) 38.11 | 6.34 | 10.32 | 12.10 |

(2) In 1.2 liters of water was dissolved 50.0 g of the unpurified sulfate obtained in (1). The solution was charged in 1.5 liters of HP-20, eluted with water and then eluted with a methanol-water mixture (mixing ratio, 1:1) to give 2.5 liters of the fraction containing the product. After concentrating the fraction, the concentrate was freeze dried to give 33.8 g of glutathione monoisopropyl ester.

(i) Melting point: 184–186° C.
(ii) Infrared absorption spectra (KBr, cm$^{-1}$) 1730, 1635, 1525, 1400, 1370, 1205, 1100
(iii) Specific rotary power ($[\alpha]_D^{21}$) −31.0 (c=1.0, water)
(iv) Nuclear magnetic resonance spectra (DMSO-d$_6$, δppm) 1.20 (6H, D, J=6Hz), 1.72–2.16 (2H, m), 2.20–2.40 (2H, m), 2.64–2.86 (2H, m), 3.20–3.56 (1H, m), 3.80 (2H, m), 4.20–4.60 (1H, m), 4.68–5.08 (1H, m)

What is claimed is:

1. A method for treating ischemic heat diseases in a patient in need of treatment which comprises administering to said patient a therpeutically-effective amount of a pharmaceutical composition comprised of from 30 to 5,000 mg. of a glutathione monoalkyl ester represented by the formula:

wherein R represents an alkyl group, or a salt thereof, and a pharmaceutically acceptable carrier.

2. The method of claim 1 wherein R is a lower alkyl group.

3. The method of claim 1 wherein R is an isopropyl group.